(12) United States Patent
Matsuzawa et al.

(10) Patent No.: US 12,091,421 B2
(45) Date of Patent: Sep. 17, 2024

(54) FUSED THIOPHENE MOLECULE AND p-TYPE SEMICONDUCTOR FILM AND ELECTRONIC DEVICE

(71) Applicant: Panasonic Intellectual Property Management Co., Ltd., Osaka (JP)

(72) Inventors: Nobuyuki Matsuzawa, Osaka (JP); Hideyuki Arai, Osaka (JP); Masaru Sasago, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 906 days.

(21) Appl. No.: 17/263,715

(22) PCT Filed: Aug. 7, 2019

(86) PCT No.: PCT/JP2019/031155
§ 371 (c)(1),
(2) Date: Jan. 27, 2021

(87) PCT Pub. No.: WO2020/045000
PCT Pub. Date: Mar. 5, 2020

(65) Prior Publication Data
US 2021/0371428 A1    Dec. 2, 2021

(30) Foreign Application Priority Data
Aug. 29, 2018 (JP) .............................. JP2018-160672

(51) Int. Cl.
C07D 495/14    (2006.01)
H10K 10/46     (2023.01)
H10K 85/60     (2023.01)

(52) U.S. Cl.
CPC ......... *C07D 495/14* (2013.01); *H10K 10/466* (2023.02); *H10K 85/6576* (2023.02)

(58) Field of Classification Search
CPC . C07D 495/14; H10K 10/466; H10K 85/6576
See application file for complete search history.

(56) References Cited

U.S. PATENT DOCUMENTS

| 8,372,312 B1 | 2/2013 | Wu et al. |
| 10,629,818 B2* | 4/2020 | Koyanagi ............... C09B 57/00 |
| 2018/0062087 A1 | 3/2018 | Hamada et al. |
| 2018/0159053 A1* | 6/2018 | Koyanagi .............. H10K 85/40 |
| 2019/0048021 A1 | 2/2019 | Arai et al. |

FOREIGN PATENT DOCUMENTS

| EP | 3050887 | | 8/2016 |
| JP | 2007-197400 | * | 8/2007 |
| JP | 2013-87118 | | 5/2013 |
| JP | 6318452 B | | 5/2018 |
| WO | 2016/152889 | | 9/2016 |
| WO | 2017/150474 | | 9/2017 |

OTHER PUBLICATIONS

Tan, Chem Sci, 2012, vol. 3, 2530-2541. (Year: 2012).*
Kruger, Adv Funct Mater, 2007, vol. 17, 3715-3723. (Year: 2007).*
English Translation of Chinese Office Action issued Feb. 3, 2023 in corresponding Chinese Patent Application No. 201980051845.4.
International Search Report of PCT application No. PCT/JP2019/031155 dated Oct. 29, 2019.
STN Registry File, Apr. 14, 2016, RN 1890206-20-8, [online], retrieved on Oct. 15, 2019.

* cited by examiner

*Primary Examiner* — D Margaret M Seaman
(74) *Attorney, Agent, or Firm* — Wenderoth, Lind & Ponack, L.L.P.

(57) ABSTRACT

To provide a fused thiophene molecule having further sufficiently high hole mobility. Disclosed is a fused thiophene molecule that has seven aromatic rings containing three thiophene rings in one molecule and in which the seven aromatic rings have one or two naphthalene structures. And, semiconductor devices including a layer using the fused thiophene molecule are disclosed.

7 Claims, 2 Drawing Sheets

FUSED THIOPHENE MOLECULE AND p-TYPE SEMICONDUCTOR FILM AND ELECTRONIC DEVICE

FIELD OF THE INVENTION

The present disclosure relates to a fused thiophene molecule, a p-type semiconductor film and an electronic device.

DESCRIPTION OF THE RELATED ART

In recent years, many electronic devices using organic materials as materials forming semiconductor layers (semiconductor films), especially thin film transistors (Thin Film Transistor, TFTs), have been proposed, and researches and developments thereof have been vigorously carried out. There are various advantages to using organic materials for the semiconductor layer. For example, while conventional inorganic thin film transistors based on inorganic amorphous silicon or the like require a heating process of about 350° C. to 400° C., organic TFTs can be manufactured by a low temperature heating process of about 50° C. to 200° C. Thus, it is possible to fabricate an element on a base having a lower heat resistance such as a plastic film. Further, it is also an advantage of organic materials that a large area device can be manufactured at a low cost by forming a semiconductor layer by using an easy forming method such as a spin coating method, an inkjet method, or printing.

One of indices used for determining a performance of a TFT is carrier mobility of a semiconductor layer, and many studies have been made to improve the carrier mobility of an organic semiconductor layer (organic semiconductor film) in an organic TFT. Of these studies, the studies that focuses on molecules of an organic material forming an organic semiconductor layer (organic semiconductor film) include, for example, a study using a fused thiophene molecule having a structure in which four to nine aromatic rings containing two thiophene rings are condensed in one molecule (PTLs 1 to 3), and a study using a fused thiophene molecule having a structure in which eight to thirteen aromatic rings containing four thiophene rings are condensed in one molecule (PTL 4). As described above, achieving an organic semiconductor having good properties and achieving a film of such an organic semiconductor lead to improvement in performances of electronic devices. For that purpose, it is necessary to study on further improvement of the properties of organic semiconductors and films of such organic semiconductors.

In particular, as a p-type organic semiconductor material of a fused thiophene molecule, benzothieno-benzothiophene (BTBT) and derivatives (C8-BTBT) of the benzothieno-benzothiophene are known to have high carrier mobility.

CITATION LIST

Patent Literature

PTL 1: International Publication No. 2017/150474
PTL 2: International Publication No. 2016/152889
PTL 3: Japanese Patent No. 6318452
PTL 4: European Patent Publication No. 3050887

SUMMARY OF THE INVENTION

The inventors of the present disclosure found that new issues as shown below would occur with conventional p-type organic semiconductor materials.

Since it cannot be said that the hole mobility of the conventionally known fused thiophene molecule is sufficiently high, it has not been possible to obtain an electronic device having a sufficiently high operation speed.

Specifically, molecular-based materials such as BTBT and derivatives of BTBT have hole mobility of at most about 5 to 10 $cm^2/Vs$. In this case, an element having a gate length of 10 μm has an operation speed of at most about 1 MHz. Almost the lower limit of the gate length formable by a coating method is 1 μm, and even such an element has an operation speed of at most about 10 MHz. Thus, to achieve an operation speed of about 100 MHz, which is necessary for Radio Frequency Identifications (RF-ID), an organic semiconductor material having higher hole mobility has been required.

An object of the present disclosure is to provide a fused thiophene molecule having further sufficiently high hole mobility, a p-type semiconductor film containing the fused thiophene molecule, and an electronic device using the p-type semiconductor film.

The present disclosure provides a fused thiophene molecule that has, in one molecule, seven aromatic rings containing three thiophene rings and in which the seven aromatic rings have one or two naphthalene structures, a p-type semiconductor film containing the fused thiophene molecule, and an electronic device using the p-type semiconductor film.

Since the fused thiophene molecule of the present disclosure exhibits further sufficiently high hole mobility, a p-type semiconductor film containing the fused thiophene molecule can improve frequency characteristics of an electronic device.

DETAILED DESCRIPTION OF THE PREFERRED EMBODIMENTS

[Fused Thiophene Molecule]

Figure 1:
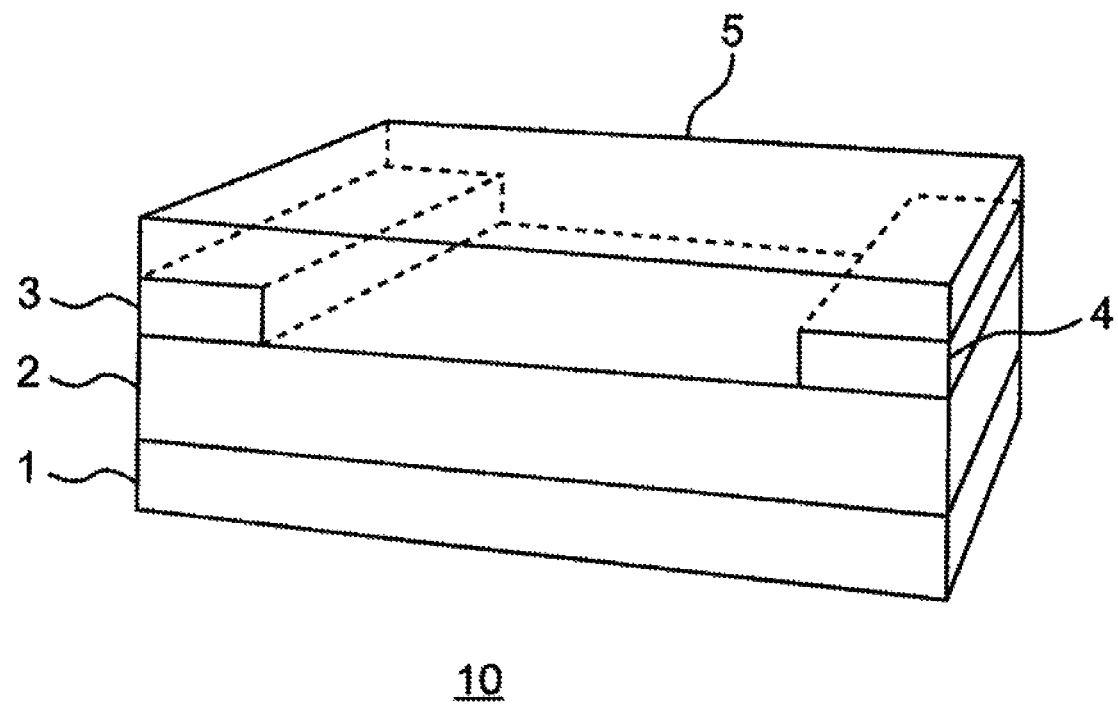
FIG. 1 is a schematic structural diagram showing an example of a basic structure of a transistor using a fused thiophene molecule of the present disclosure.

The fused thiophene molecule of the present disclosure has a structure in which seven aromatic rings containing three thiophene rings are condensed in one molecule. The thiophene ring belongs to the aromatic ring. The aromatic ring other than the thiophene ring contained in the fused thiophene molecule of the present disclosure is usually a benzene ring. Therefore, the seven aromatic rings of the fused thiophene molecule of the present disclosure usually contain three thiophene rings and four benzene rings in a condensed form. Condensation refers to the fact that two adjacent aromatic rings have two carbon atoms and a bond (i.e., a covalent bond) formed therebetween, and a state thereof.

When the fused thiophene molecule contains two or less or four thiophene rings, a sufficiently high hole mobility cannot be obtained.

Even if the fused thiophene molecule contains three thiophene rings, when the number of aromatic rings (including the thiophene ring) constituting the fused thiophene molecule is not seven, a sufficiently high hole mobility cannot be obtained.

In the present disclosure, an aromatic ring portion (i.e., aromatic ring condensation portion) composed of seven aromatic rings has a linear structure. Specifically, the aromatic ring portion is a portion in which seven aromatic rings are condensed in a chemical structural formula. The fused thiophene molecule of the present disclosure has such an aromatic ring portion, and may further have a substituent if desired. The fact that such an aromatic ring portion has the linear structure means that the aromatic ring portion does not have a branched structure in its chemical structural formula and has a structure forming a single linear shape as a whole. That is, all the aromatic rings constituting the aromatic ring portion are condensed with only one or two adjacent aromatic rings, respectively, and have a linear structure as a whole. The seven aromatic rings constituting the aromatic ring portion having the linear structure do not include any aromatic ring condensed with three or more adjacent aromatic rings. If even one aromatic ring condensed with three or more adjacent aromatic rings is contained in the seven aromatic rings constituting the aromatic ring portion, the aromatic ring portion can be regarded as having a branched structure.

In the aromatic ring portion having the linear structure, each of the two terminal aromatic rings is an aromatic ring that is condensed with only one adjacent aromatic ring. The two terminal aromatic rings may be each independently a benzene ring or thiophene rings. When the terminal aromatic ring is a thiophene ring, the thiophene ring is condensed with only one adjacent aromatic ring so as to share the following carbon atoms: the carbon atoms at the second and third positions in the thiophene ring, the carbon atoms at the third and fourth positions, or the carbon atoms at the fourth and fifth positions. The first position in the thiophene ring is usually the position of the sulfur atom.

On the other hand, each of the aromatic rings other than the two terminal aromatic rings is an aromatic ring that is condensed with only two adjacent aromatic rings. The aromatic rings other than the two terminal aromatic rings may be each independently a benzene ring or thiophene ring.

In the aromatic ring portion having the linear structure, among the aromatic rings other than the two terminal aromatic rings, when the benzene ring is condensed with one adjacent aromatic ring so as to share the carbon atoms at the first and second positions in the benzene ring, each of all the aromatic rings that are benzene rings is condensed with the other adjacent aromatic ring so as to share the following carbon atoms: the carbon atoms at the third and fourth positions in the benzene ring, the carbon atoms at the fourth and fifth positions, or the carbon atoms at the fifth and sixth positions (preferably the carbon atoms at the fourth and fifth positions).

In the aromatic ring portion having the linear structure, among the aromatic rings other than the two terminal aromatic rings, when the thiophene ring is condensed with one adjacent aromatic ring so as to share the carbon atoms at the second and third positions in the thiophene ring, each of all the aromatic rings that are thiophene rings is condensed with the other adjacent aromatic ring so as to share the following carbon atoms: the carbon atoms at the fourth and fifth positions in the thiophene ring.

The fused thiophene molecule of the present disclosure has one or two naphthalene structures in one molecule. The fact that the fused thiophene molecule of the present disclosure has one or two naphthalene structures in one molecule means that the aromatic ring portion of the fused thiophene molecule of the present disclosure has, in its chemical structural formula, one or two portions in which two benzene rings are continuously condensed. The number of naphthalene structures are calculated so that any benzene ring belonging to two or more naphthalene structures is not generated.

Even if the fused thiophene molecule contains three thiophene rings and four benzene rings, when the fused thiophene molecule does not have any naphthalene structure, a sufficiently high hole mobility cannot be obtained. Since a higher hole mobility can be obtained by molecular stacking in the naphthalene structure, a sufficiently high hole mobility cannot be obtained in a molecule without a naphthalene structure.

The fused thiophene molecule of the present disclosure preferably has two naphthalene structures in one molecule from the point of view of higher hole mobility.

In the aromatic ring portion of the fused thiophene molecule of the present disclosure, from the point of view of higher hole mobility, at least one of the two terminal aromatic rings is preferably a thiophene ring, and more preferably, both aromatic rings are thiophene rings.

Although the aromatic ring portion of the fused thiophene molecule of the present disclosure may or may not have symmetry, from the point of view of a reduction in a manufacturing cost based on synthesis easiness, and higher hole mobility, the aromatic ring portion preferably has so-called $C_2$, $C_{2V}$ or $C_{2h}$ or higher-order symmetry.

Specific examples of the fused thiophene molecule of the present disclosure include compounds represented by the following general formulas (I), (II), (III) and (IV).

The compound of the general formula (I) is a fused thiophene molecule having an aromatic ring portion having a linear structure and has C2V symmetry.

The compound of the general formula (II) is a fused thiophene molecule having the aromatic ring portion having the linear structure and does not have any symmetry.

The compound of the general formula (III) is a fused thiophene molecule having the aromatic ring portion having the linear structure and does not have any symmetry.

The compound of the general formula (IV) is a fused thiophene molecule having the aromatic ring portion having the linear structure and does not have any symmetry.

[CHEM. 1]

(I)

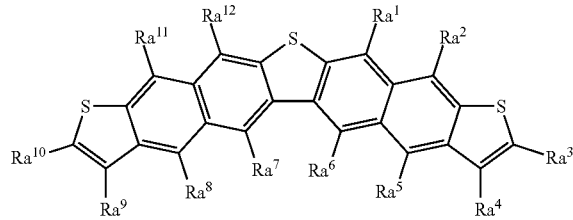

In the general formula (I), $Ra^1$ to $Ra^{12}$ (i.e., $Ra^1$, $Ra^2$, $Ra^3$, $Ra^4$, $Ra^5$, $Ra^6$, $Ra^7$, $Ra^8$, $Ra^9$, $Ra^{10}$, $Ra^{11}$, and $Ra^{12}$) are each independently a hydrogen atom, an alkyl group having 1 to 20 carbon atoms, preferably 1 to 10 carbon atoms, and more preferably 3 to 8 carbon atoms, or an aryl group having 6 to 18 carbon atoms, and preferably 6 to 12 carbon atoms. At least one group of $Ra^1$ to $Ra^{12}$ (for example, $Ra^3$ and $Ra^{10}$) is preferably an alkyl group or aryl group from the point of view of solubility of the fused thiophene molecule in an organic solvent and higher hole mobility (at this time, the other group is a hydrogen atom). Examples of the alkyl group in $Ra^1$ to $Ra^{12}$ include methyl group, ethyl group, n-propyl, isopropyl group, n-butyl group, isobutyl group, sec-butyl group, tert-butyl group, pentyl group, hexyl group, heptyl group, octyl group, nonyl group, decyl group and the like. Examples of the aryl group in $Ra^1$ to $Ra^{12}$ include a phenyl group (Ph), a naphthyl group, a 4-biphenyl group, a 3-biphenyl group, a 2-biphenyl group and the like.

In the general formula (I), in a preferred embodiment, each group is as follows: $Ra^1$, $Ra^2$, $Ra^4$ to $Ra^9$, $Ra^{11}$ and $Ra^{12}$ are each independently a hydrogen atom or an alkyl group having 1 to 10 carbon atoms, and more preferably a hydrogen atom. $Ra^3$ and $Ra^{10}$ are each independently a hydrogen atom, an alkyl group having 1 to 10 carbon atoms, or an aryl group having 6 to 18 carbon atoms, and more preferably a hydrogen atom, an alkyl group having 3 to 8 carbon atoms, or an aryl group having 6 to 12 carbon atoms, and still more preferably a hydrogen atom.

Specific examples of the compound represented by the general formula (I) include the compounds shown in the following table.

[CHEM. 2]

(II)

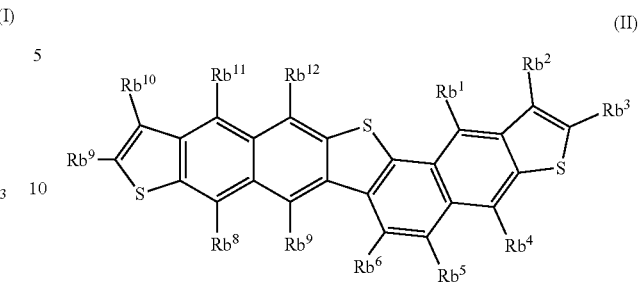

In the general formula (II), $Rb^1$ to $Rb^{12}$ (i.e., $Rb^1$, $Rb^2$, $Rb^3$, $Rb^4$, $Rb^5$, $Rb^6$, $Rb^7$, $Rb^8$, $Rb^9$, $Rb^{10}$, $Rb^{11}$ and $Rb^{12}$) are each independently a hydrogen atom, an alkyl group having 1 to 20 carbon atoms, preferably 1 to 10 carbon atoms, and more preferably 3 to 8 carbon atoms, or an aryl group having 6 to 18 carbon atoms, and preferably 6 to 12 carbon atoms. At least one group of $Rb^1$ to $Rb^{12}$ (for example, $Rb^3$ and $Rb^9$) is preferably an alkyl group or aryl group from the point of view of solubility of the fused thiophene molecule in an organic solvent and higher hole mobility (at this time, the other group is a hydrogen atom). Examples of the alkyl group in $Rb^1$ to $Rb^{12}$ include the same alkyl group exemplified as the alkyl group in $Ra^1$ to $Ra^{12}$. Examples of the aryl group in $Rb^1$ to $Rb^{12}$ include the same aryl group exemplified as the aryl group in $Ra^1$ to $Ra^{12}$.

In the general formula (II), in a preferred embodiment, each group is as follows: $Rb^1$, $Rb^2$, $Rb^4$ to $Rb^8$, and $Rb^{10}$ to $Rb^{12}$ are each independently a hydrogen atom or an alkyl group having 1 to 10 carbon atoms, and more preferably a hydrogen atom. $Rb^3$ and $Rb^9$ are each independently a hydrogen atom, an alkyl group having 1 to 10 carbon atoms, or an aryl group having 6 to 18 carbon atoms, and more preferably a hydrogen atom, an alkyl group having 3 to 8 carbon atoms, or an aryl group having 6 to 12 carbon atoms, and still more preferably a hydrogen atom.

Specific examples of the compound represented by the general formula (II) include the compounds shown in the following table.

TABLE 1A

Specific examples of compound of general formula (I)

| Compound | $Ra^1$ | $Ra^2$ | $Ra^3$ | $Ra^4$ | $Ra^5$ | $Ra^6$ | $Ra^7$ | $Ra^8$ | $Ra^9$ | $Ra^{10}$ | $Ra^{11}$ | $Ra^{12}$ |
|---|---|---|---|---|---|---|---|---|---|---|---|---|
| i-1 | H | H | H | H | H | H | H | H | H | H | H | H |
| i-2 | H | H | $C_8H_{17}$ | H | H | H | H | H | H | $C_8H_{17}$ | H | H |
| i-3 | H | H | Ph | H | H | H | H | H | H | Ph | H | H |
| i-4 | H | H | $C_8H_{17}$ | H | H | H | H | H | H | Ph | H | H |
| i-5 | H | H | 4-biphenyl group | H | H | H | H | H | H | 4-biphenyl group | H | H |
| i-6 | H | H | 4-biphenyl group | H | H | H | H | H | H | Ph | H | H |

TABLE 1B

Specific examples of compound of general formula (II)

| Compound | $Rb^1$ | $Rb^2$ | $Rb^3$ | $Rb^4$ | $Rb^5$ | $Rb^6$ | $Rb^7$ | $Rb^8$ | $Rb^9$ | $Rb^{10}$ | $Rb^{11}$ | $Rb^{12}$ |
|---|---|---|---|---|---|---|---|---|---|---|---|---|
| ii-1 | H | H | H | H | H | H | H | H | H | H | H | H |
| ii-2 | H | H | $C_8H_{17}$ | H | H | H | H | H | $C_8H_{17}$ | H | H | H |
| ii-3 | H | H | Ph | H | H | H | H | H | Ph | H | H | H |
| ii-4 | H | H | $C_8H_{17}$ | H | H | H | H | H | Ph | H | H | H |
| ii-5 | H | H | Ph | H | H | H | H | H | $C_8H_{17}$ | H | H | H |
| ii-6 | H | H | 4-biphenyl group | H | H | H | H | H | 4-biphenyl group | H | H | H |

[CHEM. 3]

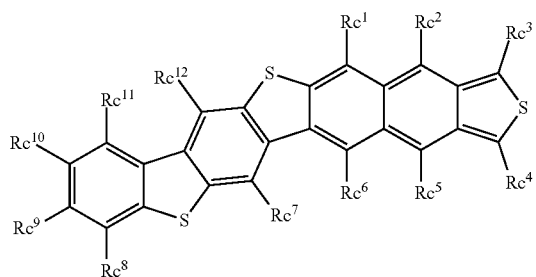

(III)

[CHEM. 4]

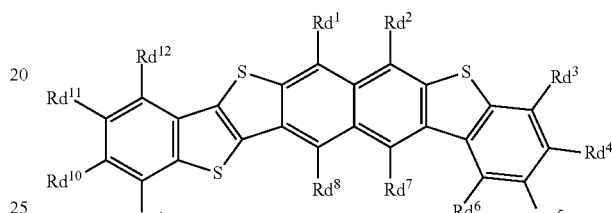

(IV)

In the general formula (III), $Rc^1$ to $Rc^{12}$ (i.e., $Rc^1$, $Rc^2$, $Rc^3$, $Rc^4$, $Rc^5$, $Rc^6$, $Rc^7$, $Rc^8$, $Rc^9$, $Rc^{10}$, $Rc^{11}$ and $Rc^{12}$) are each independently a hydrogen atom, an alkyl group having 1 to 20 carbon atoms, preferably 1 to 10 carbon atoms, and more preferably 3 to 8 carbon atoms, or an aryl group having 6 to 18 carbon atoms, and preferably 6 to 12 carbon atoms. At least one group of $Rc^1$ to $Rc^{12}$ (for example, $Rc^3$ and $Rc^4$) is preferably an alkyl group or aryl group, and more preferably alkyl group from the point of view of solubility of the fused thiophene molecule in an organic solvent and higher hole mobility (at this time, the other group is a hydrogen atom). Examples of the alkyl group in $Rc^1$ to $Rc^{12}$ include the same alkyl group exemplified as the alkyl group in $Ra^1$ to $Ra^{12}$. Examples of the aryl group in $Rc^1$ to $Rc^{12}$ include the same aryl group exemplified as the aryl group in $Ra^1$ to $Ra^{12}$.

In the general formula (III), in a preferred embodiment, each group is as follows: $Rc^1$, $Rc^2$, and $Rc^5$ to $Rc^{12}$ are each independently a hydrogen atom or an alkyl group having 1 to 10 carbon atoms, and more preferably a hydrogen atom. $Rc^3$ and $Rc^4$ are each independently a hydrogen atom, an alkyl group having 1 to 10 carbon atoms, or an aryl group having 6 to 18 carbon atoms, and more preferably a hydrogen atom, an alkyl group having 3 to 8 carbon atoms, or an aryl group having 6 to 12 carbon atoms, and most preferably a hydrogen atom.

Specific examples of the compound represented by the general formula (III) include the compounds shown in the following table.

In the general formula (IV), $Rd^1$ to $Rd^{12}$ (i.e., $Rd^1$, $Rd^2$, $Rd^3$, $Rd^4$, $Rd^5$, $Rd^6$, $Rd^7$, $Rd^8$, $Rd^9$, $Rd^{10}$, $Rd^{11}$ and $Rd^{12}$) are each independently a hydrogen atom, an alkyl group having 1 to 20 carbon atoms, preferably 1 to 10 carbon atoms, and more preferably 3 to 8 carbon atoms, or an aryl group having 6 to 18 carbon atoms, and preferably 6 to 12 carbon atoms. At least one group of $Rd^1$ to $Rd^{12}$ (for example, $Rd^4$ and $Rd^{10}$) is preferably an alkyl group or aryl group, and more preferably alkyl group from the point of view of solubility of the fused thiophene molecule in an organic solvent and higher hole mobility (at this time, the other group is a hydrogen atom). Examples of the alkyl group in $Rd^1$ to $Rd^{12}$ include the same alkyl group exemplified as the alkyl group in $Ra^1$ to $Ra^{12}$. Examples of the aryl group in $Rd^1$ to $Rd^{12}$ include the same aryl group exemplified as the aryl group in $Ra^1$ to $Ra^{12}$.

In the general formula (IV), in a preferred embodiment, each group is as follows: $Rd^1$ to $Rd^3$, $Rd^5$ to $Rd^9$, and $Rd^{11}$ to $Rd^{12}$ are each independently a hydrogen atom or an alkyl group having 1 to 10 carbon atoms, and more preferably a hydrogen atom. $Rd^4$ and $Rd^{10}$ are each independently a hydrogen atom, an alkyl group having 1 to 10 carbon atoms, or an aryl group having 6 to 18 carbon atoms, and more preferably a hydrogen atom, an alkyl group having 3 to 8 carbon atoms, or an aryl group having 6 to 12 carbon atoms, and most preferably a hydrogen atom.

Specific examples of the compound represented by the general formula (IV) include the compounds shown in the following table.

TABLE 1C

Specific examples of compound of general formula (III)

| Compound | $Rc^1$ | $Rc^2$ | $Rc^3$ | $Rc^4$ | $Rc^5$ | $Rc^6$ | $Rc^7$ | $Rc^8$ | $Rc^9$ | $Rc^{10}$ | $Rc^{11}$ | $Rc^{12}$ |
|---|---|---|---|---|---|---|---|---|---|---|---|---|
| iii-1 | H | H | H | H | H | H | H | H | H | H | H | H |
| iii-2 | H | H | $C_8H_{17}$ | $C_8H_{17}$ | H | H | H | H | H | H | H | H |
| iii-3 | H | H | Ph | Ph | H | H | H | H | H | H | H | H |

TABLE 1D

Specific examples of compound of general formula (IV)

| Compound | Rd$^1$ | Rd$^2$ | Rd$^3$ | Rd$^4$ | Rd$^5$ | Rd$^6$ | Rd$^7$ | Rd$^8$ | Rd$^9$ | Rd$^{10}$ | Rd$^{11}$ | Rd$^{12}$ |
|---|---|---|---|---|---|---|---|---|---|---|---|---|
| iv-1 | H | H | H | H | H | H | H | H | H | H | H | H |
| iv-2 | H | H | H | C$_8$H$_{17}$ | H | H | H | H | H | C$_8$H$_{17}$ | H | H |
| iv-3 | H | H | H | Ph | H | H | H | H | H | Ph | H | H |

[Production of Fused Thiophene Molecule]

The fused thiophene molecule can be produced by a known method.

For example, using a raw material (for example, naphthalene) constituting a portion of the aromatic ring portion of a target fused thiophene molecule, halogenation reaction (for example, iodination reaction) and Sonogashira coupling reaction of a hydrogen atom at a desired position are repeated. The desired position means a position where a condensed thiophene ring or a condensed benzene ring should be formed in order to obtain a desired fused thiophene molecule. Consequently, a condensed thiophene ring and a condensed benzene ring can be formed at the desired position, and as a result, a desired fused thiophene molecule can be produced. When an intermediate in which a hydrogen atom at a desired position is halogenated cannot be obtained alone but can be obtained as a mixture, separation and purification may be performed by a known separation method such as column chromatography.

In the Sonogashira coupling reaction for forming a condensed thiophene ring, a trimethylsilylethynyl group is introduced using trimethylsilylacetylene in a solvent in the presence of a catalyst, and then a methylthio group is introduced and refluxed at a desired position. Consequently, the trimethylsilylethynyl group reacts with the methylthio group to form a condensed thiophene ring. The introduction of the methylthio group into the desired position can be achieved by halogenation reaction (for example, iodination reaction), a reaction with dimethyl disulfide, and separation and purification performed thereafter by a known method such as column chromatography.

In the Sonogashira coupling reaction for forming a condensed benzene ring, two trimethylsilylethynyl groups are introduced into one molecule using trimethylsilylacetylene in a solvent in the presence of a catalyst. Then, a condensed benzene ring is formed by reacting (ring-closure reaction) the two trimethylsilylethynyl groups. The ring-closing reaction with two trimethylsilylethynyl groups can be achieved by, for example, adding a tellurium powder, a degassed solution containing an intermediate with two trimethylsilylethynyl groups introduced, and methyltri-n-octylammonium chloride to sodium hydroxide, sodium borohydroxide, and an aqueous solution of hydrazine monohydrate, and leaving the mixture at 40° C. to 50° C. for several hours.

[Identification of Fused Thiophene Molecule]

The fused thiophene molecule of the present disclosure can be identified by elemental analysis, mass spectrometry, and C$^{13}$—NMR (carbon-13 nuclear magnetic resonance).

That is, the elemental analysis is used to identify the atom number constituting one molecular of fused thiophene molecule, and the mass spectrometry is used to measure a molecular weight of the fused thiophene molecule, so that a molecular formula of the fused thiophene molecule can be determined.

Then, by analyzing an amount of chemical shift of each peak obtained by C$^{13}$—NMR, a structural formula of the fused thiophene molecule, a substituent and its substitution position can be identified.

[Use of Fused Thiophene Molecule]

The fused thiophene molecule of the present disclosure has a further sufficiently high hole mobility and is therefore useful as a molecule-based organic semiconductor material or a carbon-based hole transfer material, in particular, a p-type semiconductor material. Thus, when the fused thiophene molecule of the present disclosure is used for an electronic device (electronic element) such as a transistor, frequency characteristics of the electronic device can be improved.

FIG. 1 shows an example of a basic structure of a transistor using the fused thiophene molecule of the present disclosure. With reference to FIG. 1, basic transistor structure body 10 includes:

gate electrode 1;
gate insulating film 2 formed on gate electrode 1;
source electrode 3 and drain electrode 4 separately formed on gate insulating film 2; and
semiconductor film 5 formed in contact with an exposed region of gate insulating film 2 and in contact with source electrode 3 and drain electrode 4.

There is no particular limitation to a material that constitutes gate electrode 1 as long as the material is used as an electrode material in the field of electronic devices, and examples of the material include silicon, gold, copper, nickel, and aluminum.

There is no particular limitation to a material that constitutes gate insulating film 2 as long as the material has electrical insulation properties. Specific examples of the material that constitutes gate insulating film 2 include, for example: metal oxides or metal nitrides such as silicon oxide (such as SiO$_2$), silicon nitride (such as Si$_3$N$_4$), tantalum oxide (such as Ta$_2$O$_5$), aluminum oxide (such as Al$_2$O$_3$), titanium oxide (such as TiO$_2$), yttrium oxide (such as Y$_2$O$_3$), and lanthanum oxide (such as La$_2$O$_3$); nitride; and polymer materials such as epoxy resin, polyimide (PI) resin, polyphenylene ether (PPE) resin, polyphenylene oxide resin (PPO), and polyvinyl pyrrolidone (PVP) resin.

The material that constitutes source electrode 3 and drain electrode 4 may be the material exemplified as the material that constitutes gate electrode 1.

Semiconductor film 5 is a p-type semiconductor film containing the fused thiophene molecule of the present disclosure. As long as semiconductor film 5 contains the fused thiophene molecule of the present disclosure, semiconductor film 5 may contain other materials. For example, semiconductor film 5 may be constituted only by the fused thiophene molecule of the present disclosure, or may contain fullerene, perylenedimide, polythiophene, other fused thiophenes other than the fused thiophene molecule of the present disclosure. A content amount of the fused thiophene molecule of the present disclosure in semiconductor film 5 is, for example, more than or equal to 0.1 mass %, is preferably more than or equal to 1 mass %, and, from the point of view of further improvement in the hole mobility, is preferably more than or equal to 10 mass %, is more preferably more than or equal to 50 mass %, and is most preferably 100 mass %.

Semiconductor film 5 can be formed by a method similar to a known method such as a vacuum vapor deposition method or a coating method other than by using the fused thiophene molecule of the present disclosure as a semiconductor material. In this case, by using only the fused thiophene molecule as a vapor deposition material in a vacuum vapor deposition method, it is possible to form a semiconductor film having a content amount of the fused thiophene molecule of 100 mass %.

Figure 2:
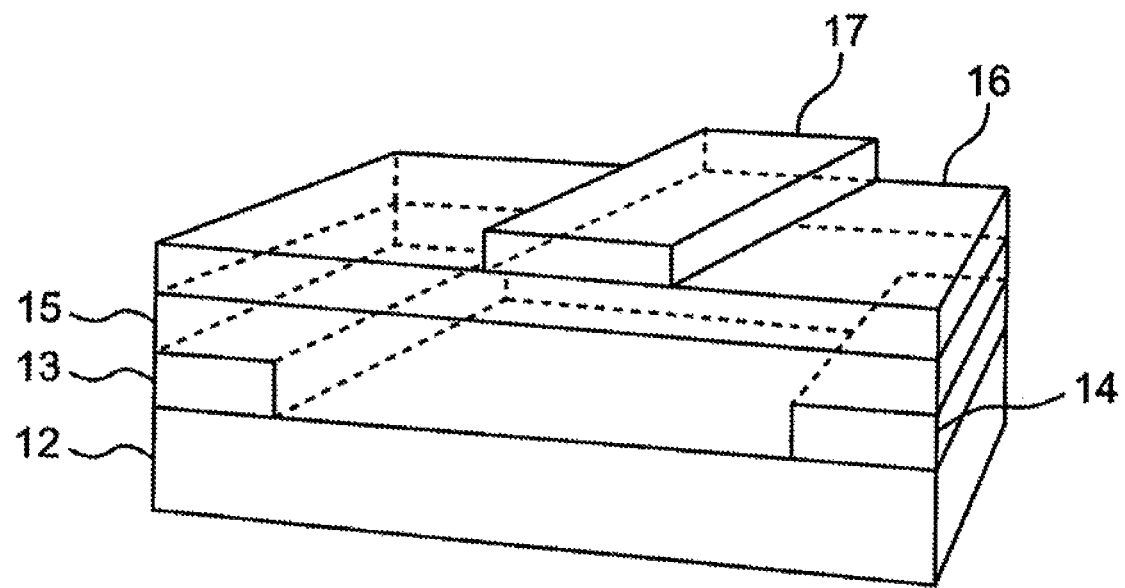
FIG. 2 is a schematic structural diagram showing another example of the basic structure of the transistor using the fused thiophene molecule of the present disclosure.

FIG. 2 shows another example of the basic structure of the transistor using the fused thiophene molecule of the present disclosure. With reference to FIG. 2, basic transistor structure body 11 includes:

base substrate 12 having insulation properties;
source electrode 13 and drain electrode 14 separately formed on base substrate 12 having insulation properties;
semiconductor film 15 formed in contact with an exposed region of base substrate 12 having insulation properties and in contact with source electrode 13 and drain electrode 14;
gate insulating film 16 formed on semiconductor film 15; and
gate electrode 17 formed at a position, on gate insulating film 16, between source electrode 13 and drain electrode 14 as viewed from above.

There is no particular limitation to the material constituting base substrate 12 having insulation properties as long as the material has electrical insulation properties. Specific examples of the material that constitutes base substrate 12 include, for example: metal oxides or metal nitrides formed on a silicon wafer such as silicon oxide (such as $SiO_2$), silicon nitride (such as $Si_3N_4$), tantalum oxide (such as $Ta_2O_5$), aluminum oxide (such as $Al_2O_3$), titanium oxide (such as $TiO_2$), yttrium oxide (such as $Y_2O_3$), and lanthanum oxide (such as $La_2O_3$); or metal nitride; and polymer materials such as epoxy resin, polyimide (PI) resin, polyphenylene ether (PPE) resin, polyphenylene oxide resin (PPO), and polyvinyl pyrrolidone (PVP) resin.

There is no particular limitation to a material that constitutes source electrode 13 and drain electrode 14 as long as the material is used as an electrode material in the field of electronic devices, and examples of the material include silicon, gold, copper, nickel, and aluminum.

Semiconductor film 15 is a p-type semiconductor film containing the fused thiophene molecule of the present disclosure. As long as semiconductor film 15 contains the fused thiophene molecule of the present disclosure, semiconductor film 15 may contain other materials. For example, semiconductor film 15 may be constituted only by the fused thiophene molecule of the present disclosure, or may contain fullerene, perylenedimide, polythiophene, other fused thiophenes other than the fused thiophene molecule of the present disclosure. A content amount of the fused thiophene molecule of the present disclosure in semiconductor film 15 is, for example, more than or equal to 0.1 mass %, is preferably more than or equal to 1 mass %, and, from the point of view of further improvement in the hole mobility, is preferably more than or equal to 10 mass %, is more preferably more than or equal to 50 mass %, and is most preferably 100 mass %.

There is no particular limitation to a material that constitutes gate insulating film 16 as long as the material has electrical insulation properties. Specific examples of the material that constitutes gate insulating film 16 include, for example: metal oxides or metal nitrides such as silicon oxide (such as $SiO_2$), silicon nitride (such as $Si_3N_4$), tantalum oxide (such as $Ta_2O_5$), aluminum oxide (such as $Al_2O_3$), titanium oxide (such as $TiO_2$), yttrium oxide (such as $Y_2O_3$), and lanthanum oxide (such as $La_2O_3$); or metal nitride; and polymer materials such as epoxy resin, polyimide (PI) resin, polyphenylene ether (PPE) resin, polyphenylene oxide resin (PPO), and polyvinyl pyrrolidone (PVP) resin.

The material that constitutes gate electrode 17 may be the material exemplified as the material that constitutes source electrode 13 and drain electrode 14.

EXAMPLE

Experimental Example I

The inventors calculated the hole mobility of fused thiophene molecule, based on molecular dynamics and molecular orbital calculation. As a calculation method of mobility, the method described in the following document was used: David Evans et al., Organic Electronics Vol. 29 (2016), pp. 50-56 (David R. Evans et al., "Estimation of charge carrier mobility in amorphous organic materials using percolation corrected random-walk method", Organic Electronics vol. 29 (2016) pages 50-56).

Specifically, a charge hopping rate (κ) required to calculate mobility is known to be given by the following equation.

[MATH. 1]
$$\kappa = \frac{2\pi}{\hbar}\left(\frac{H_{ab}^2}{\sqrt{4\pi\lambda k_B T}}\right)\exp\left(-\frac{(\Delta G + \lambda)^2}{\sqrt{4\lambda k_B T}}\right)$$

where ΔG is change in free energy upon charge transfer, λ is Marcus reorganization energy, Hab is electronic coupling between molecules, $k_B$ is Boltzmann constant, and T is temperature.

$$\hbar \qquad\qquad\qquad\qquad\text{[MATH. 2]}$$

is Planck's constant. ΔG was set to zero.

In calculation of K, 64 object molecules were disposed at random, an equilibrium state of the object molecules was calculated by molecular dynamics calculation for several 10 ns at room temperature. From the result obtained by the above calculation, 50 molecular pairs were arbitrary picked up, and K was calculated by density-functional theory for every picked-up pair.

For the above molecular dynamics calculation, the product name "Desmond" from Schrödinger, Inc., which was a package for molecular dynamics calculation, was used (Bowers et al., 2006 ACM/IEEE Bulletin of Conference on Supercomputing, Tampa, Florida, Reference No. 84) (K. J. Bowers et al. Proc. 2006 ACM/IEEE Conference on Supercomputing, ACM, Tampa, Florida, 2006 No. 84). Further, for calculation of λ and Hab, the product name "Jaguar" from Schrödinger, Inc., which was calculation software of density-functional theory, was used (Bochevalov et al., International Journal of Quantum Chemical, Vol. 113, 2013, pp. 2110-2142 (A. D. Bochevarov et al., Intl. J. Quantum Chem. Vol. 113 (2013) p. 2110-2142)).

In this way, calculation by a density-functional theory was performed for each molecular pair to obtain 50 K's values, and to calculate mobility from these values, a method considering percolation described in the above literature of Evans et al. (Organic Electronics Vol. 29 (2016), pp. 50-56) was used.

Specifically, mobility $\mu_{h,p}(p)$ was calculated by the following equation. In the equation, e is an elementary charge.

[MATH. 3]

$$\mu_{h,p}(p) = \frac{eD_p}{k_B T} \times \theta(p)$$

Further, $D_p$ is given by the equation below.

[MATH. 4]

$$D_p = \frac{1}{2n}\sum_i D_{h,i} P_i (D_{h,i} \geq D_{th} \text{ for all } i)$$

$P_i$ is given by the equation below.

[MATH. 5]

$$P_i = \frac{\kappa_i}{\Sigma_i \kappa_i}$$

Further, $D_{h,i}$ is given by the equation below.

[MATH. 6]

$$D_{h,i} = \frac{1}{2n} r_i^2 \kappa_i$$

Note that i is a number assigned to each molecular pair. The value $r_i$ is a distance between molecules in the i-th molecular pair.

In addition, the value $D_t h$ represents an amount satisfying the equation below.

[MATH. 7]

$$D_p \theta(p) \leq D_{th} \quad (A)$$

In addition, $\theta(p)$ is given by the equation below.

[Math. 8]

$$\theta(p) = \left(\frac{p - p_c}{1 - p_c}\right)^\nu \quad (B)$$

$D_{th}$ was self-consistently determined from Equations (A) and (B). Further, $P_c$ is 0.3116, and $\nu$ is 2.

By this method, the hole mobilities (cm²/Vs) of compounds (i-1), (ii-1), (iii-1), and (iv-1) as fused thiophene molecules were calculated. The calculated values are shown below. The calculated values are relative values when the calculated value of the hole mobility of BTBT (compound (x-1)) is 1.

TABLE 2A

| | Example |
|---|---|
| Compound | Relative value of hole mobility |
| i-1 | 1.9 |
| ii-1 | 1.8 |
| iii-1 | 1.8 |
| iv-1 | 1.5 |

The hole mobilities (cm²/Vs) of the following compounds (x-1) to (x-7) were calculated by the same method as above. The calculated values are shown below. These calculated values are also relative values when the calculated value of the hole mobility of BTBT is 1. The compound (x-1) corresponds to BTBT.

[CHEM. 5]

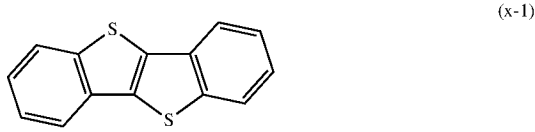
(x-1)

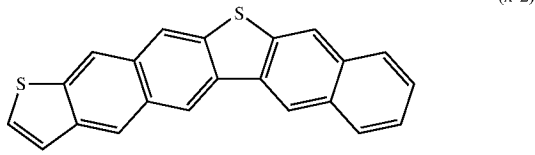
(x-2)

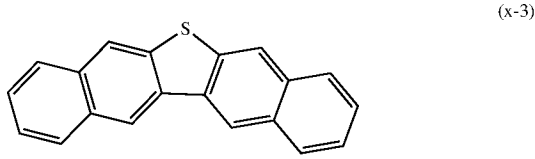
(x-3)

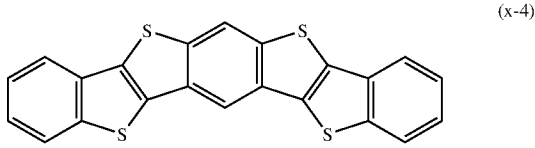
(x-4)

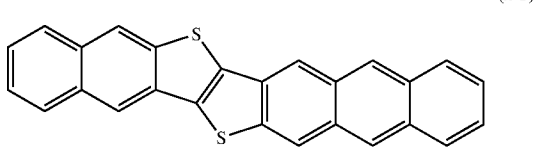
(x-5)

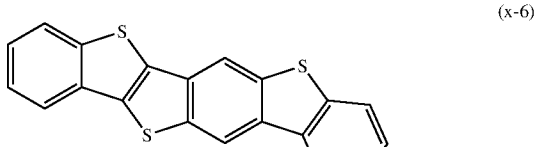
(x-6)

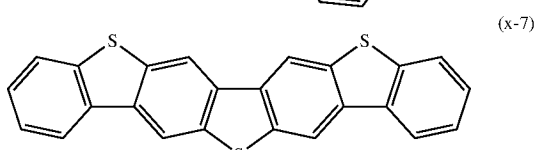
(x-7)

TABLE 2B

| Comparative Example | |
|---|---|
| Compound | Relative value of hole mobility |
| x-1 | 1.0 |
| x-2 | 0.8 |
| x-3 | 0.9 |
| x-4 | 0.7 |
| x-5 | 1.2 |
| x-6 | 1.1 |
| x-7 | 1.2 |

As shown in Tables 2A and 2B, it has been found that the fused thiophene molecule of the present disclosure exhibits further sufficiently high hole mobility.

The relative value of the hole mobility calculated in this Experimental Example I is very close to the actually measured hole mobility.

<Experimental Example II> (Production of Compound (i-1))

Specifically, a mixture of naphthalene iodide was synthesized by heating and reducing commercially available naphthalene with iodine and nitric acid. This mixture was separated and purified by column chromatography (hexane/dichloromethane=1/3) to synthesize the following 2,7-diiodonaphthalene.

[CHEM. 6]

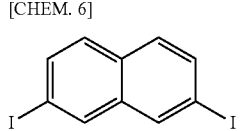

This compound was reacted with trimethylsilylacetylene (purchased from Tokyo Chemical Industry Co., Ltd.), bis(triphenylphosphine)palladium(II) dichloride (purchased from Tokyo Chemical Industry Co., Ltd.) and copper iodide (purchased from Sigma-Aldrich Company Limited Liability Company (Sigma-Aldrich Co., LLC.)) in a mixed solvent of diethylamine and tetrahydrofuran. As a result, the following compound was synthesized based on the Sonogashira coupling reaction.

[CHEM. 7]

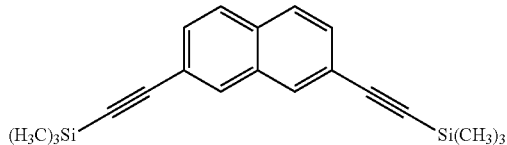

The above compound was treated with bromine gas. In addition, to a dimethylformamide (DMF) solution of the mixture after treatment, a pentane solution of tert-butyllithium (Sigma-Aldrich Company Limited Liability Company) was added at −78° C., and the mixed solution was gradually returned to room temperature. Then, dimethyl disulfide (Tokyo Chemical Industry Co., Ltd.) was added, and the obtained mixture was separated and purified by column chromatography (hexane/dichloromethane=1/3) to obtain the following compound.

[CHEM. 8]

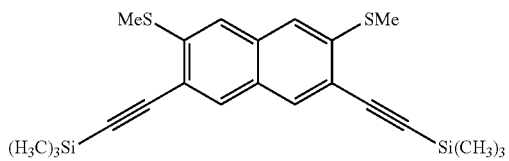

The dichloromethane solution of the above compound was refluxed, and in addition, an iodine powder was added thereto. Then, in an environment of −10° C., a dichloromethane solution of iodine chloride was added to the dichloromethane solution, and the mixture was left at room temperature for about half a day to obtain the following compound.

[CHEM. 9]

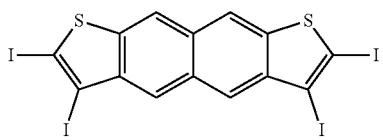

In addition, by irradiating the above dichloromethane solution with ultraviolet light (365 nm), deiodination reaction was promoted, and the following compound was obtained.

[CHEM. 10]

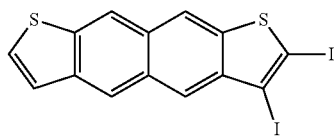

This compound was reacted with trimethylsilylacetylene (purchased from Tokyo Chemical Industry Co., Ltd.), bis(triphenylphosphine)palladium(II) dichloride (purchased from Tokyo Chemical Industry Co., Ltd.) and copper iodide (purchased from Sigma-Aldrich Company Limited Liability Company) in a mixed solvent of diethylamine and tetrahydrofuran to obtain the following reaction product based on the Sonogashira coupling reaction.

[CHEM. 11]

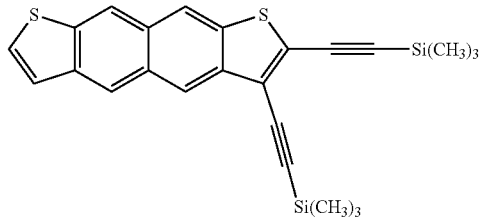

Next, to sodium hydroxide (purchased from Tokyo Chemical Industry Co., Ltd.), sodium borohydroxide (purchased from Tokyo Chemical Industry Co., Ltd.), and an aqueous solution of hydrazine monohydrate (purchased from Sigma-Aldrich Company Limited Liability Company), a tellurium powder (purchased from Kojundo Chemical Laboratory Co., Ltd.) was added. Then, after degassing treatment, Aliquat 336 (purchased from Sigma-Aldrich Company Limited Liability Company) was added, and left at 45° C. for several hours to purify a product precipitate, and thus to obtain the following compound.

[CHEM. 12]

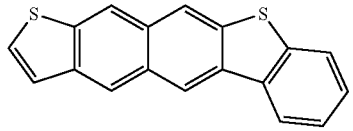

In addition, a material prepared by heating and reducing this compound with iodine and nitric acid was separated and purified by column chromatography (hexane-dichloromethane=1:3) to obtain a compound described below.

[CHEM. 13]

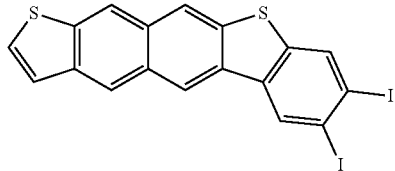

This compound was reacted with trimethylsilylacetylene (purchased from Tokyo Chemical Industry Co., Ltd.), bis(triphenylphosphine)palladium(II) dichloride (purchased from Tokyo Chemical Industry Co., Ltd.) and copper iodide (purchased from Sigma-Aldrich Company Limited Liability Company) in a mixed solvent of diethylamine and tetrahydrofuran to obtain the following reaction product based on the Sonogashira coupling reaction.

[CHEM. 14]

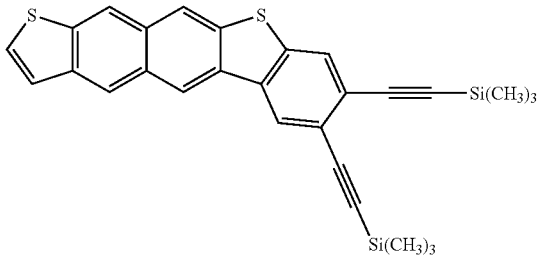

Next, to sodium hydroxide (purchased from Tokyo Chemical Industry Co., Ltd.), sodium borohydroxide (purchased from Tokyo Chemical Industry Co., Ltd.), and an aqueous solution of hydrazine monohydrate (purchased from Sigma-Aldrich Company Limited Liability Company), a tellurium powder (purchased from Kojundo Chemical Laboratory Co., Ltd.) was added. Then, after degassing treatment, Aliquat 336 (purchased from Sigma-Aldrich Company Limited Liability Company) was added, and left at 45° C. for several hours to purify a product precipitate, and thus to obtain the following compound.

[CHEM. 15]

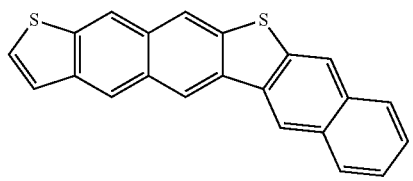

By heating and reducing this compound with iodine and nitric acid, a mixture of iodide of the compound was obtained, and this mixture was separated and purified by column chromatography (hexane/dichloromethane=1/3) to obtain a compound described below.

[CHEM. 16]

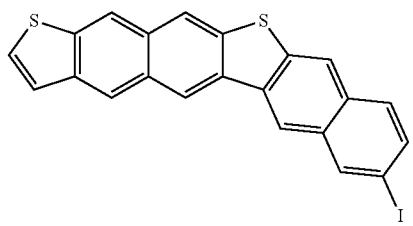

This compound was reacted with trimethylsilylacetylene (purchased from Tokyo Chemical Industry Co., Ltd.), bis(triphenylphosphine)palladium(II) dichloride (purchased from Tokyo Chemical Industry Co., Ltd.) and copper iodide (purchased from Sigma-Aldrich Company Limited Liability Company) in a mixed solvent of diethylamine and tetrahydrofuran to obtain a reaction product based on the Sonogashira coupling reaction. The reaction product was treated with bromine gas, and, in addition, the prepared compound was separated and purified by column chromatography (hexane/dichloromethane=1/3) to obtain a compound described below.

[CHEM. 17]

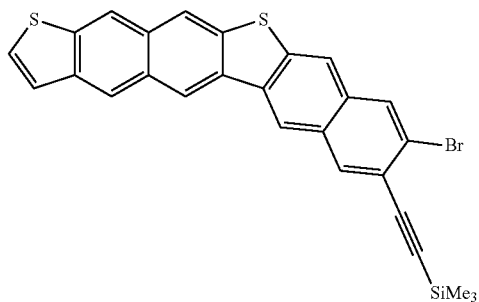

To a DMF solution of the above compound, a pentane solution of tert-butyllithium (Sigma-Aldrich Company Limited Liability Company) was added at −78° C., and the solution was gradually returned to room temperature. Then, dimethyl disulfide (Tokyo Chemical Industry Co., Ltd.) was added to obtain a reaction product. The dichloromethane solution of the reaction product was refluxed, and, in addition, an iodine powder was added thereto. In addition, in an environment of −10° C., a dichloromethane solution of iodine chloride was added, and the mixture was left at room temperature for about half a day to obtain the following compound.

[CHEM. 18]

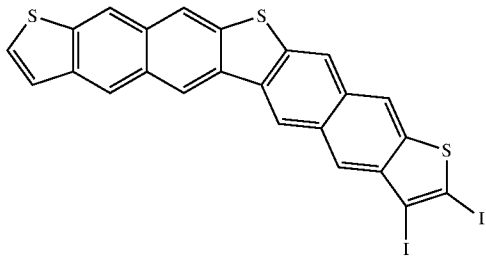

Finally, by irradiating the above dichloromethane solution with ultraviolet light (365 nm), deiodination reaction was promoted, and the following compound (i-1) was obtained.

[CHEM. 19]

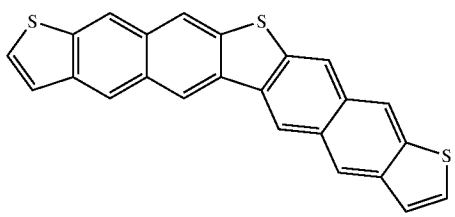

(i-1)

The formation of the compound (i-1) was confirmed by the following analysis: •carbon/hydrogen/sulfur analysis C:S:H=8:1:4 •Mass spectrometry; 396.55

Example 1 and Comparative Example 1

The basic transistor structure body 11 shown in FIG. 2 was manufactured using the compound (i-1) or the compound (x-1). Specifically, an oxide film having a film thickness of 350 nm was formed on a silicon wafer by a thermal oxidation process using an oxidation diffusion furnace. On the oxide film, gold electrodes (having a thickness of 100 nm) having a 5 μm gap between the gold electrodes were formed by a lift-off method. In addition, a film was formed on the gold electrodes by a vacuum vapor deposition method such that the organic molecule (Example 1: compound (i-1), Comparative Example 1: BTBT (commercially available product) of compound (x-1)) whose mobility was to be measured had a thickness of 200 nm. Subsequently, a silicon nitride film having a thickness of 100 nm was formed as an insulating layer. Thereafter, a third electrode was formed on the silicon nitride film by a lift-off method so as to be disposed inside the 5 μm clearance between the gold electrodes when viewed from an upper surface. In Example 1, the content of the compound (i-1) in an organic molecular film was 100 mass % with respect to a total amount of the film. In Comparative Example 1, the content of the compound (x-1) in the organic molecular film was 100 mass % with respect to the total amount of the film.

The thus manufactured transistor structure was used to measure the mobility. It is known that the mobility is given by the equation below.

[MATH. 9]

$$\sqrt{I_d} = \sqrt{\frac{\mu W C_i}{2L}} (V_g - V_{th})$$

where $I_d$ is a drain current, μ is mobility, W is a channel width, L is a channel length, $C_i$ is a capacitance of a gate insulating film per unit area, $V_g$ is a gate voltage, and $V_{th}$ is a threshold voltage. It can be seen that the mobility can be obtained by measuring a dependency of the drain current on the gate voltage by the above equation.

The hole mobility of the film (Example 1) of the fused thiophene molecular compound (i-1) measured by the above method was 20 cm²/Vs. On the other hand, the hole mobility of the film (Comparative Example 1) of the compound (x-1) was 11 cm²/Vs.

As described above, it can be seen that the fused thiophene molecule of the present disclosure exhibits a sufficiently higher hole mobility than the conventional fused thiophene molecule even by actual measurement. It can be seen that the relative value of the hole mobility calculated in Experimental Example I is very close to the hole mobilities of Example 1 and Comparative Example 1 actually measured in this Experimental Example II.

INDUSTRIAL APPLICABILITY

The fused thiophene molecule of the present disclosure has a further sufficiently high hole mobility and is therefore useful as a molecule-based organic semiconductor material or a carbon-based hole transfer material, in particular, a p-type semiconductor material. Thus, the fused thiophene molecule of the present disclosure is useful for electronic devices or electronic elements, such as transistors. The fused thiophene molecule of the present disclosure can improve the frequency characteristics of an electronic device.

The invention claimed is:

1. A fused thiophene molecule comprising seven aromatic rings containing three thiophene rings in one molecule, wherein the seven aromatic rings have one or two naphthalene structures, and
wherein the fused thiophene molecule is represented by a general formula (III) or (IV) provided as follows:

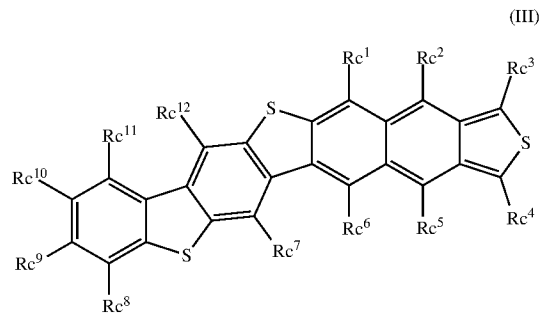

(III)

in the general formula (III), $Rc^1$ to $Rc^{12}$ are each independently a hydrogen atom, an alkyl group having 1 to 20 carbon atoms, or an aryl group having 6 to 18 carbon atoms,

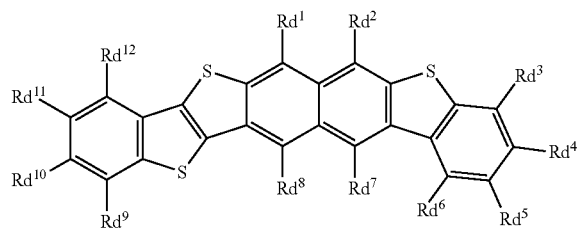

(IV)

in the general formula (IV), $Rd^1$ to $Rd^{12}$ are each independently a hydrogen atom, an alkyl group having 1 to 20 carbon atoms, or an aryl group having 6 to 18 carbon atoms.

2. The fused thiophene molecule according to claim 1, wherein
the seven aromatic rings are condensed with each other to form an aromatic ring portion, and
the aromatic ring portion has a linear structure.

3. The fused thiophene molecule according to claim 2, wherein, in the aromatic ring portion of the seven aromatic rings, at least one of the two aromatic rings at an end of the linear structure is a thiophene ring.

4. The fused thiophene molecule according to claim 1, wherein
the seven aromatic rings are condensed with each other to form an aromatic ring portion, and
the aromatic ring portion has $C_2$, $C_{2v}$, $C_{2h}$, or higher-order symmetry.

5. A p-type semiconductor film comprising the fused thiophene molecule according to claim 1.

6. An electronic device comprising the p-type semiconductor film according to claim 5.

7. An electronic device comprising a transistor including a source electrode, a drain electrode, a gate electrode, and a semiconductor film,
wherein the semiconductor film is the p-type semiconductor film according to claim 5.

* * * * *